United States Patent [19]

Bolanos et al.

[11] Patent Number: 5,560,530
[45] Date of Patent: Oct. 1, 1996

[54] GRADUATED ANVIL FOR SURGICAL STAPLING INSTRUMENTS

[75] Inventors: Henry Bolanos, East Norwalk; Randolph F. Lehn, Stratford, both of Conn.

[73] Assignee: United States Surgical Corporation, Norwalk, Conn.

[21] Appl. No.: 533,534

[22] Filed: Sep. 25, 1995

Related U.S. Application Data

[63] Continuation of Ser. No. 224,361, Apr. 7, 1994, abandoned.

[51] Int. Cl.⁶ ................................. A61B 17/068
[52] U.S. Cl. .................. 227/176.1; 227/180.1; 227/19
[58] Field of Search .................. 227/19, 180.1, 227/175.1, 176.1

[56] References Cited

U.S. PATENT DOCUMENTS

| | | |
|---|---|---|
| D. 272,851 | 2/1984 | Green et al. . |
| D. 278,080 | 3/1985 | Green et al. . |
| D. 284,698 | 7/1986 | Green . |
| 3,079,606 | 3/1963 | Bobrov et al. . |
| 3,317,105 | 5/1967 | Astafjev et al. ............... 227/19 |
| 3,490,675 | 1/1970 | Green et al. . |
| 3,499,591 | 3/1970 | Green . |
| 4,290,542 | 9/1981 | Fedotov et al. ............... 227/19 |
| 4,491,133 | 1/1985 | Menges et al. ............... 227/19 |
| 4,633,874 | 1/1987 | Chow et al. . |
| 4,784,137 | 11/1988 | Kulik et al. ............... 227/180 |
| 5,040,715 | 8/1991 | Green et al. . |
| 5,083,695 | 1/1992 | Foslien et al. ............... 227/19 |
| 5,263,629 | 11/1993 | Trumbull et al. ............... 227/19 |

FOREIGN PATENT DOCUMENTS

| | | |
|---|---|---|
| 0179623 | 4/1986 | European Pat. Off. . |
| 0491537 | 6/1992 | European Pat. Off. . |

OTHER PUBLICATIONS

Information Booklet for Auto Suture® Multifire Endo GIA™ 30 Disposable Surgical Stapler (Apr., 1991, Auto Suture Co., a division of United States Surgical Corporation).

*Primary Examiner*—Scott A. Smith

[57] ABSTRACT

An anvil is disclosed for utilization in conjunction with a surgical stapling instrument configured to apply rows of staples to body tissue. The anvil is provided with graduations to delineate the boundaries of the staple forming area defined thereby, as well as to delineate the range through which a fastener driving assembly and optional knife blade translate during a stapling operation.

12 Claims, 4 Drawing Sheets

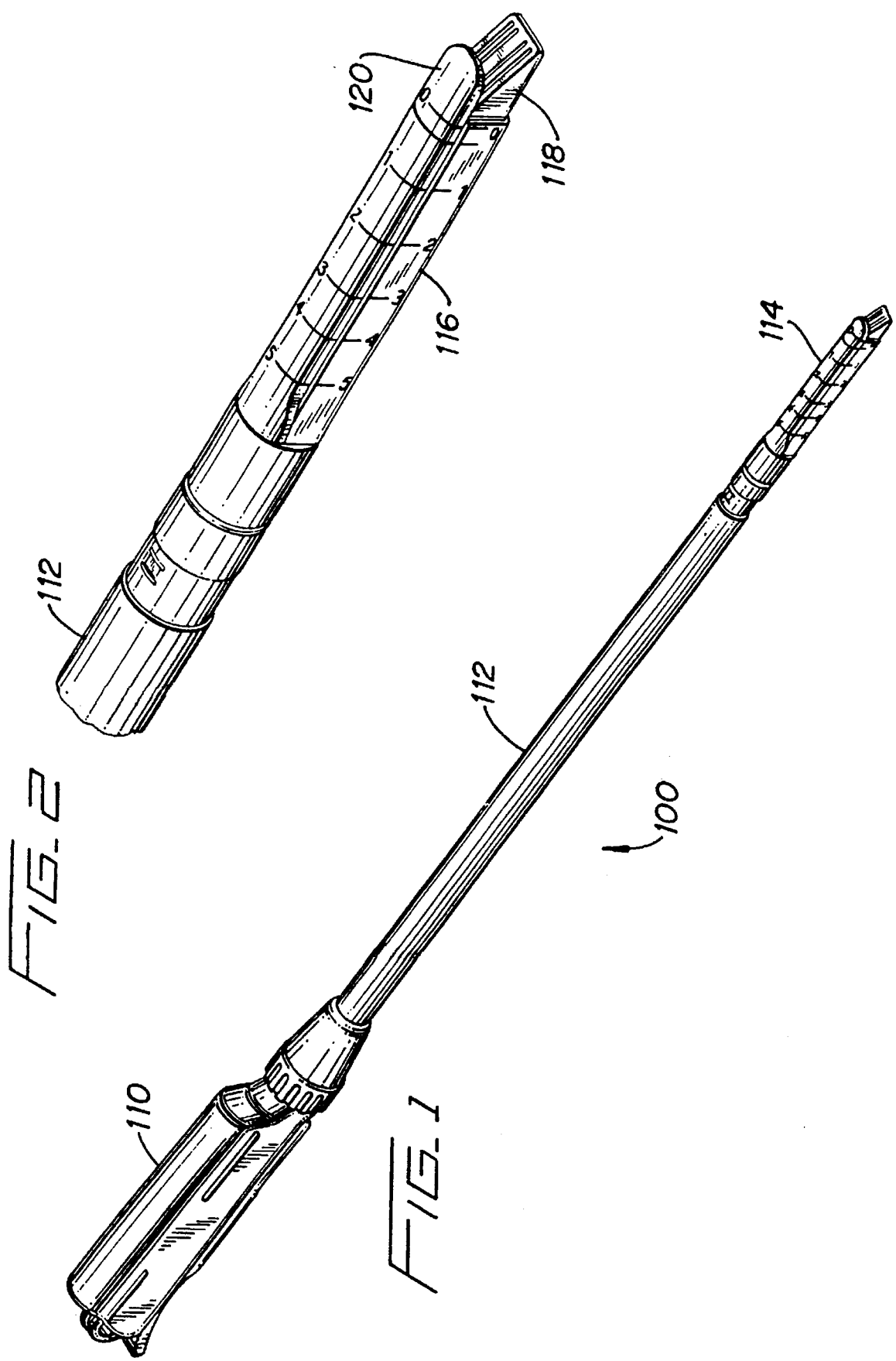

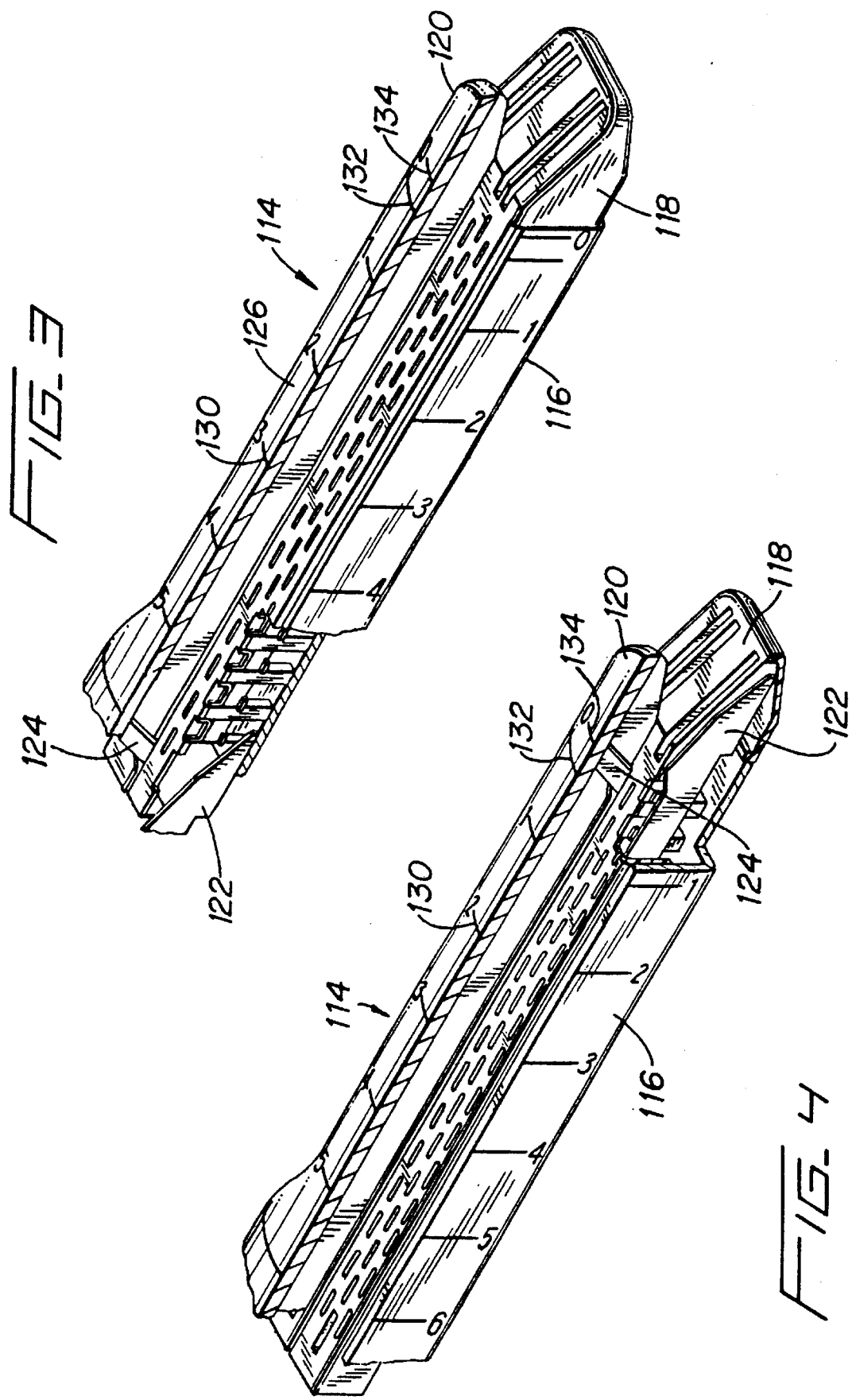

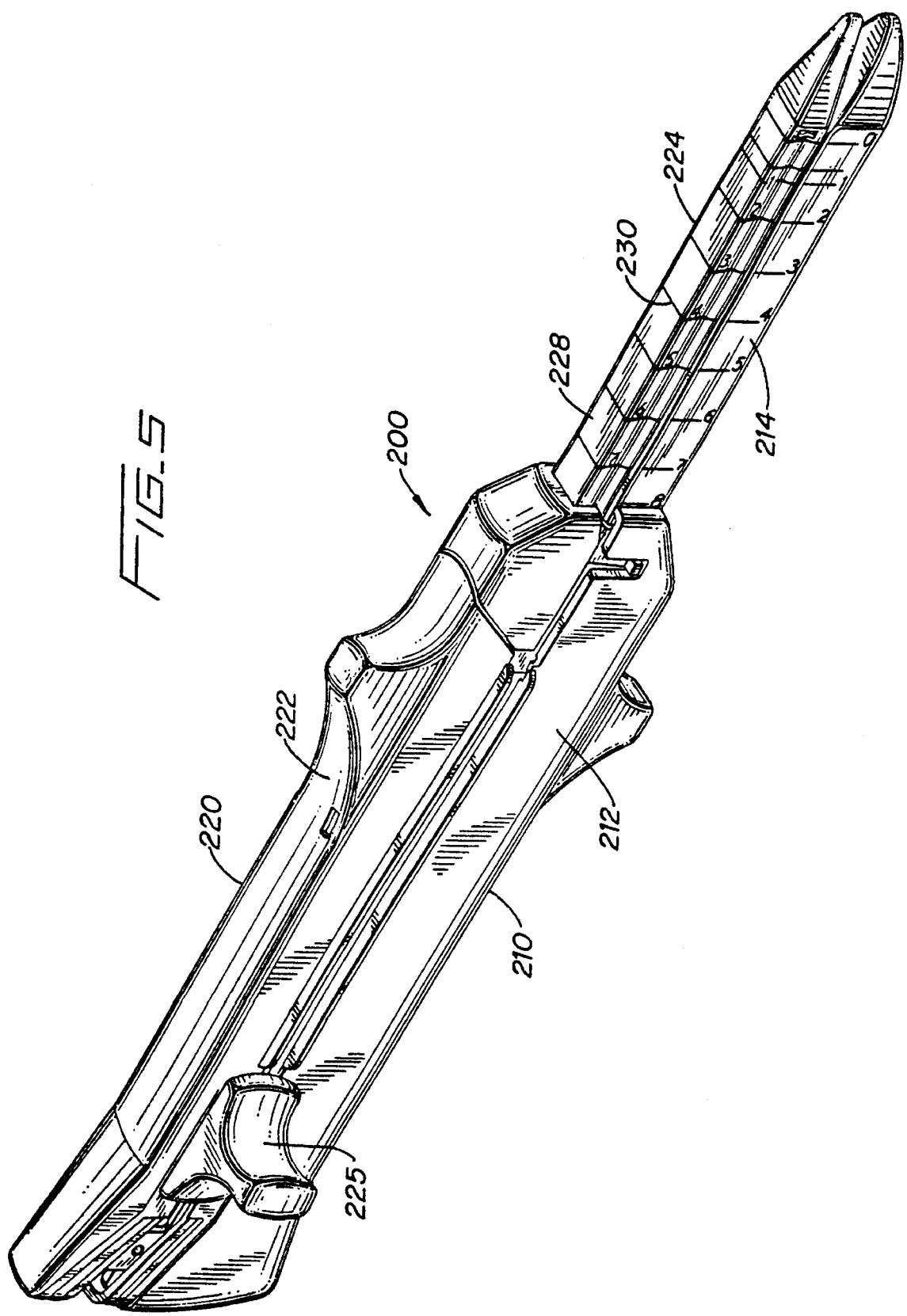

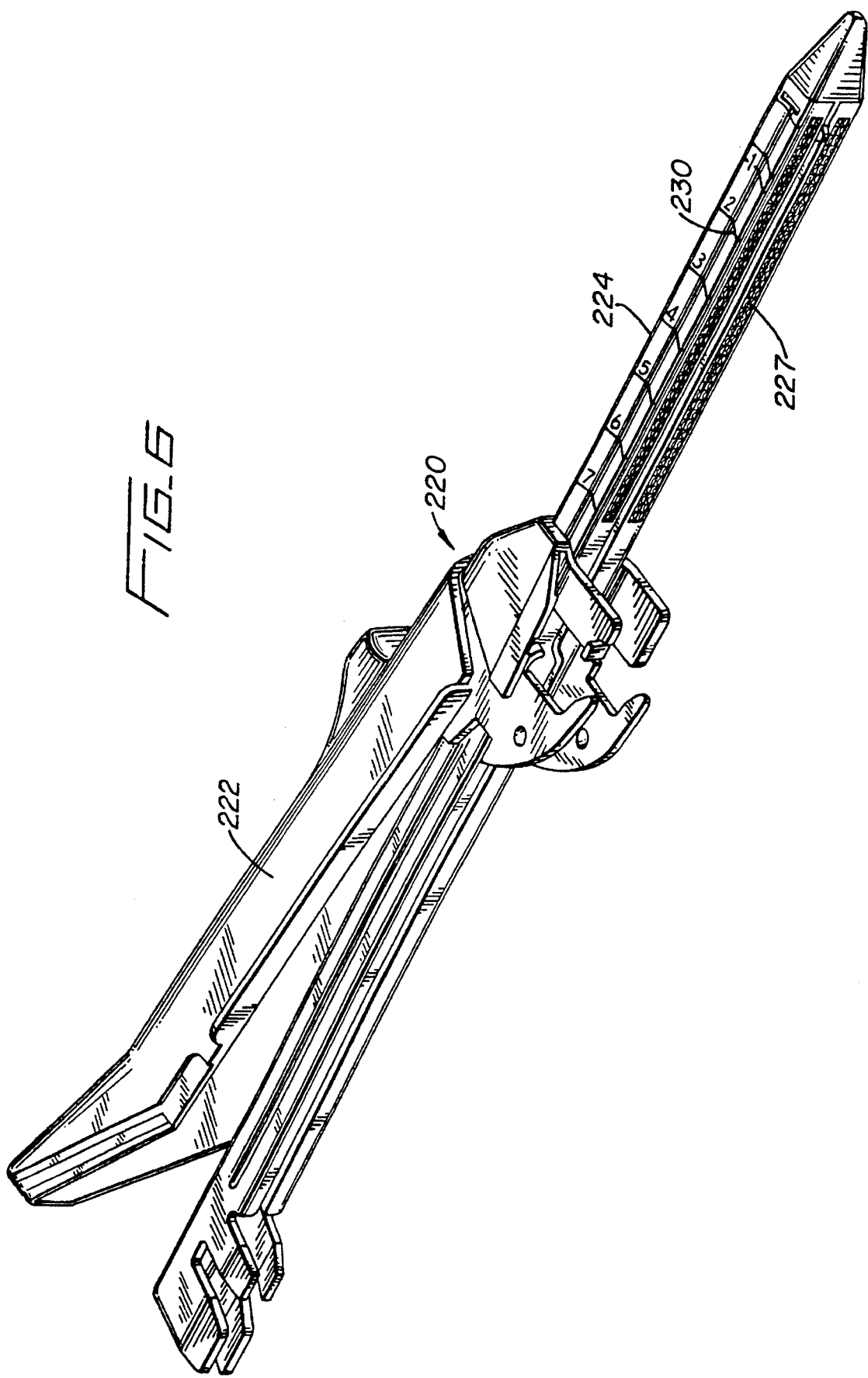

GRADUATED ANVIL FOR SURGICAL STAPLING INSTRUMENTS

This is a continuation of application Ser. No. 08/224,361, filed on Apr. 7, 1994, now abandoned.

BACKGROUND

1. Field of the Invention

This invention relates to surgical stapling instruments, and more particularly, to a graduated anvil for surgical stapling instruments configured to sequentially apply a plurality of surgical fasteners to body tissue and optionally incise the fastened tissue.

2. Description of Related Art

Surgical stapling devices wherein tissue is first grasped or clamped between opposing jaw structure and then joined by means of surgical fasteners are well known in the art. In some instruments a knife is provided to cut the tissue which has been joined by the fasteners. The fasteners are typically in the form of surgical staples or two part polymeric fasteners.

Instruments for this purpose can comprise two elongated members which are respectively used to capture or clamp tissue. Typically, one of the members carries a disposable cartridge which houses a plurality of staples arranged in at least two lateral rows while the other member comprises an anvil which defines a surface for forming the staple legs as the fasteners are driven from the cartridge. Generally, the stapling operation is effected by a pusher which travels longitudinally through the cartridge carrying member, with the pusher acting upon the staples to sequentially eject them from the cartridge. A knife may be associated with the pusher between the staple rows to longitudinally cut and/or open the tissue disposed between the rows of staples. Such instruments are disclosed, for example, in commonly assigned U.S. Pat. Nos. 3,079,606, 3,490,675 and 5,014,899.

A later stapler disclosed in U.S. Pat. No. 3,499,591 to Green applies a double row of staples on each side of the incision. This is accomplished by providing a cartridge assembly in which a cam member moves through an elongate guide path between two sets of staggered staple carrying grooves. Staple drive members are located within the grooves and are positioned in such a manner so as to be contacted by the longitudinally moving cam to effect ejection of the staples.

Each of the instruments described above were designed for use in open surgical procedures wherein surgeons have direct manual access to the operative site. However, in endoscopic or laparoscopic procedures, surgery is performed through a small incision or through narrow cannulae inserted through small entrance wounds in the skin. In order to address the specific needs of endoscopic and/or laparoscopic surgical procedures, an endoscopic surgical stapling apparatus has been developed and is disclosed in U.S. Pat. No. 5,040,715 to Green et al. This apparatus is well suited for such procedures and includes a fastener applying assembly having an anvil and a staple cartridge provided at the distal end of an endoscopic portion which permits the instrument to be inserted into a cannula and be remotely operated by the surgeon through manipulation of a proximal handle mechanism.

During the performance of a surgical stapling procedure, it is necessary for the surgeon to be well aware of the dimensional limitations of the instrument which they are using. For example, when tissue is to be stapled and cut, the surgeon must be able to accurately position the tissue within the jaws of the apparatus to ensure the tissue will be properly stapled and cut. In the past, markings have been imprinted on the cartridge carrying member of such stapling instruments. See, for example, U.S. Pat. Nos. 4,633,874, Des. 272,851, Des. 278,080 and Des. 284,698. However, during certain procedures, the instruments may be oriented in a position where the cartridge carrying member is blocked from the surgeon's view.

Accordingly, there is a need in the art for an anvil having graduations or markings provided thereon to delineate the dimensions of the instrument such as the boundaries of the staple forming area formed on the anvil, the range through which the knife blade travels to cut tissue, and/or the range through which the staple driving member travels to eject staples from the cartridge. The present invention describes both conventional and laparoscopic surgical stapling instruments having graduated anvils to serve these needs.

SUMMARY

The present invention is directed to an anvil for a surgical stapling instrument. More particularly, the invention provides a graduated anvil for a stapling device configured to sequentially apply at least two rows of staples to body tissue and to optionally cut the tissue between the rows of staples.

In a preferred embodiment of the invention, the anvil defines first and second opposed surfaces, with the first surface defining a staple forming area against which staples are driven. At least two spaced apart graduations are provided on the second surface of the anvil to delineate the boundaries of the staple forming area on the first surface of the anvil.

In another embodiment of the subject invention, at least two spaced apart graduations are provided on the anvil to delineate a range through which a knife blade translates to cut tissue. In yet another embodiment of the subject invention, graduations are provided on the anvil to delineate a range through which a staple driving assembly translates to eject staples from the cartridge.

Further features of the subject invention will become more readily apparent to those having ordinary skill in the art to which this invention pertains from the following detailed description of the invention taken in conjunction with the drawings.

BRIEF DESCRIPTION OF THE DRAWINGS

So that one skilled in the art to which the subject invention pertains will better understand how to make and use the invention, preferred embodiments of the invention will be described hereinbelow with reference to the drawings wherein:

FIG. 1 is a perspective view of a surgical stapling instrument configured for utilization in laparoscopic surgical procedures which includes a graduated anvil constructed in accordance with a preferred embodiment of the subject invention;

FIG. 2 is an enlarged perspective view of the fastener applying assembly of the surgical stapling instrument of FIG. 1, illustrating the graduations provided on the anvil;

FIG. 3 is an enlarged perspective view in cross-section of the fastener applying assembly of the surgical instrument shown in FIG. 1, with the staple driving assembly and knife blade disposed in a pre-fired proximal position;

FIG. 4 is an enlarged perspective view in cross-section of the fastener applying assembly of the surgical instrument shown in FIG. 1 with the stapling driving assembly and knife blade disposed in a post-fired distal position;

FIG. 5 is a perspective view of a surgical stapling instrument configured for utilization in open surgical procedures which includes a graduated anvil constructed in accordance with a preferred embodiment of the subject invention;

FIG. 6 is an enlarged perspective view of the fastener applying assembly of the surgical instrument shown in FIG. 5, illustrating the staple forming surface defined on the anvil.

DETAILED DESCRIPTION OF THE PREFERRED EMBODIMENTS

Referring now to the drawings wherein like reference numerals indicate similar structural features of the subject invention, there is illustrated in FIGS. 1 and 5 two surgical stapling instruments 100 and 200, which include a graduated anvil constructed in accordance with preferred embodiments of the subject invention.

Referring to FIG. 1, surgical stapler 100 is adapted and configured for utilization during endoscopic or laparoscopic procedures wherein surgery is performed through a small incision or entrance wound formed in a patients body. More particularly, during laparoscopic procedures, surgical stapler 100 can be extended through a trocar or cannula device into the abdominal cavity of a patient to sequentially apply a plurality of surgical fasteners to body tissue, and, concomitantly incise the fastened tissue. Surgical stapler 100 includes a handle assembly 110, an elongate body 112 which extends distally from handle assembly 110, and a fastener applying assembly 114 which is operatively associated with a distal end portion of elongate body 112.

Referring to FIGS. 2–4, fastener applying assembly 114 includes a cartridge housing 116 configured to support a staple carrying cartridge 118, and an anvil 120 mounted adjacent cartridge housing 116 which defines a staple forming surface (not shown) against which surgical fasteners are driven when they are ejected from cartridge 118. As best seen in FIGS. 3 and 4, a fastener driving mechanism 122 is operatively associated with staple cartridge 118 and is configured to translate through cartridge 118, in a longitudinal direction, to sequentially eject the surgical fasteners therefrom and drive them against the staple forming surface of anvil 120. A knife blade 124 is associated with fastener driving mechanism 122 and is configured to translate through cartridge 118 in conjunction therewith to form an incision in the body tissue situated between the parallel rows of staples applied thereto. In operation, the fastener driving mechanism 122 and the knife blade 124 translate together from the pre-fired proximal position illustrated in FIG. 3 to the post-fired distal position illustrated in FIG. 4.

As best seen in FIG. 2, the outer surface 126 of anvil 120 is provided with a series of graduations or markings 130 which correspond to particular linear dimensions of the anvil 120. More particularly, as illustrated in FIGS. 3 and 4, graduations 130 serve to delineate the range through which the fastener driving mechanism 122 travels during a stapling operation. The graduations provide a user with the capability to determine, from a remote point of observation (utilizing a laparoscope), the specific operating range of the staple driving mechanism 122.

The graduations are defined by linear markings coupled with numerical indicia. Preferably, the graduations are spaced in 10mm intervals and the numerical indicia decrease in magnitude in a distal direction. An additional linear marking 132 is preferably provided adjacent to the distal-most graduation 134 to indicate the distal-most boundary of the range through which the knife blade 124 travels during a stapling operations. The linear markings which define the graduations can be imprinted on the outer surface 126 of anvil 120 utilizing inking, painting or staining methods common in the art, or, in the alternative, the markings can be etched into the outer surface 126 of anvil 120.

Referring to FIG. 5, surgical stapler 200 is adapted and configured for utilization during open surgical procedures wherein surgery is performed through a radical incision formed in the patients body. This surgical stapler is also configured to sequentially apply a plurality of surgical fasteners to body tissue. In general, surgical stapler 200 has a two-part construction including a cartridge half-section 210 and an anvil half-section 220. The proximal portion 212 of cartridge half-section 210 and the proximal portion 222 of anvil half-section 220 define a handle assembly including an actuation mechanism 225. The distal portion 214 of cartridge half-section 210 and the distal portion 224 of anvil half-section 220 define a fastener applying assembly.

Referring to FIG. 6, the distal portion 224 of anvil half-section 220 defines a staple forming surface 227 against which surgical fasteners are driven and formed when ejected from the distal portion 214 of cartridge half-section 210. Staple forming surface 227 includes a plurality of staple forming cups 226 disposed in parallel rows and extending substantially along the length of the distal portion 224 of anvil half-section 220. The outer surface 228 of distal portion 224 is provided with a series of graduations or markings 230 which serve to delineate the linear boundaries of staple forming surfaces 227 and permit visual observation of these boundaries from a location remote from the surgical site. Accordingly, a surgeon using surgical stapler 200 will have the capability to properly orient the apparatus to ensure that the target tissue is adequately disposed within the boundaries of staple forming surface 227, thereby reducing the likelihood that the target tissue will be fastened incompletely. As in the preferred embodiment of FIG. 1, markings on graduations on the anvil portion preferably correspond to those provided on the cartridge portion.

Graduations 230 are preferably accompanied by corresponding numerical indicia and are preferably disposed in 10mm intervals with the indicia decreasing in magnitude in a distal direction. As in the previous embodiment, the graduations and the indicia may be imprinted on or etched into the outer surface 228 of distal portion 224.

Although the graduated anvil of the subject invention has been described with respect to a preferred embodiment, it is apparent that changes or modifications may be made thereto without departing from the spirit or scope of the invention as defined by the appended claims.

What is claimed is:

1. In a surgical apparatus configured to apply at least two parallel rows of staples to body tissue, the apparatus including a cartridge housing a plurality of staples, an anvil mounted adjacent the cartridge against which the staples are driven when ejected from the cartridge, and a staple driving assembly which translates through the cartridge to eject the staples therefrom, the improvement comprising:

at least two visible spaced apart graduations provided on each of the anvil and the cartridge to delineate a range through which the staple driving assembly translates to eject staples from the cartridge.

2. A surgical apparatus as recited in claim 1, wherein the anvil defines a longitudinal axis and the at least two spaced apart graduations define linear markings extending transverse to the longitudinal axis of the anvil.

3. A surgical apparatus as recited in claim 1, wherein the spaced apart graduations are etched into the anvil.

4. A surgical apparatus as recited in claim 1, wherein the spaced apart graduations are imprinted on of the anvil.

5. A surgical apparatus as recited in claim 1, wherein the anvil is detachably mounted adjacent the cartridge.

6. A surgical apparatus as recited in claim 1, wherein each of the spaced apart graduations have associated therewith corresponding numerical indicia.

7. A surgical apparatus as recited in claim 1, wherein the anvil has first and second opposed surfaces, the first surface defining a staple forming area against which staples are driven and second surface having said at least two spaced apart graduations disposed thereon.

8. In a surgical apparatus configured to apply at least two parallel rows of staples to body tissue, the apparatus including a staple carrying cartridge and an anvil mounted adjacent the cartridge and having a staple forming area against which staples are driven when ejected from the cartridge, the improvement comprising:

a multiplicity of visible spaced apart graduations provided on each of the anvil and the staple carrying cartridge to delineate boundaries of the staple forming area.

9. A surgical apparatus as recited in claim 8 wherein the anvil and the staple carrying cartridge each define a longitudinal axis in substantially parallel alignment, the multiplicity of graduations provided on the anvil define linear markings extending transverse to the longitudinal axis of the anvil, and the multiplicity of graduations provided on the staple carrying cartridge define linear markings extending transverse to the longitudinal axis of the staple carrying cartridge.

10. In a surgical apparatus configured to apply at least two parallel rows of staples to body tissue, the apparatus including a staple carrying cartridge and an anvil mounted adjacent the cartridge and having a staple forming area against which staples are driven when ejected from the cartridge, the anvil and the staple carrying cartridge each defining a longitudinal axis in substantially parallel alignment, the improvement comprising:

a multiplicity of visible spaced apart linear markings provided on and extending transverse to the longitudinal axis of each of the anvil and the staple carrying cartridge to delineate boundaries of the staple forming area, at least two of the linear markings on the longitudinal axis of the staple carrying cartridge corresponding to the longitudinal positions of at least two of the linear markings on the longitudinal axis of the anvil.

11. A surgical apparatus as recited in claim 10 wherein the staple carrying cartridge and the anvil have the same number of linear markings, all the linear markings on the longitudinal axis of the staple carrying cartridge corresponding to the longitudinal positions of all the linear markings on the longitudinal axis of the anvil.

12. In a surgical apparatus configured to apply at least two parallel rows of staples to body tissue, the apparatus including a staple carrying cartridge housing a plurality of staples, an anvil mounted adjacent the cartridge against which the staples are driven when ejected from the cartridge, the anvil defining a longitudinal axis substantially parallel to a longitudinal axis defined by the cartridge, and a staple driving assembly which translates through the cartridge to eject the staples therefrom, the improvement comprising:

at least two visible spaced apart linear markings provided on, and extending transverse to the longitudinal axis defined by, each of the anvil and the cartridge to delineate a range through which the staple driving assembly translates to eject staples from the cartridge, at least two of the linear markings on the longitudinal axis of the cartridge corresponding to the longitudinal positions of at least two of the linear markings on the longitudinal axis of the anvil.

* * * * *